(12) United States Patent
Atala et al.

(10) Patent No.: US 9,415,076 B2
(45) Date of Patent: Aug. 16, 2016

(54) MUSCLE TISSUE REGENERATION USING MUSCLE FIBER FRAGMENTS

(75) Inventors: Anthony Atala, Winston Salem, NC (US); James Yoo, Winston Salem, NC (US); In Kap Ko, Clemmons, NC (US)

(73) Assignee: Wake Forest University Health Sciences, Winston-Salem, NC (US)

( * ) Notice: Subject to any disclaimer, the term of this patent is extended or adjusted under 35 U.S.C. 154(b) by 240 days.

(21) Appl. No.: 14/239,416

(22) PCT Filed: Aug. 15, 2012

(86) PCT No.: PCT/US2012/050879
§ 371 (c)(1),
(2), (4) Date: May 6, 2014

(87) PCT Pub. No.: WO2013/025766
PCT Pub. Date: Feb. 21, 2013

(65) Prior Publication Data
US 2014/0242125 A1    Aug. 28, 2014

Related U.S. Application Data

(60) Provisional application No. 61/524,626, filed on Aug. 17, 2011.

(51) Int. Cl.
| | |
|---|---|
| A61K 35/34 | (2015.01) |
| A61K 45/06 | (2006.01) |
| A61K 47/34 | (2006.01) |
| A61K 47/42 | (2006.01) |
| A61K 38/18 | (2006.01) |
| A61L 27/18 | (2006.01) |
| A61L 27/24 | (2006.01) |
| A61L 27/36 | (2006.01) |
| A61L 27/38 | (2006.01) |
| A61K 9/00 | (2006.01) |

(52) U.S. Cl.
CPC .............. *A61K 35/34* (2013.01); *A61K 38/18* (2013.01); *A61K 45/06* (2013.01); *A61K 47/34* (2013.01); *A61K 47/42* (2013.01); *A61L 27/18* (2013.01); *A61L 27/24* (2013.01); *A61L 27/3604* (2013.01); *A61L 27/3683* (2013.01); *A61L 27/3834* (2013.01); *A61K 9/0034* (2013.01); *A61L 2300/414* (2013.01); *A61L 2400/06* (2013.01); *A61L 2430/30* (2013.01)

(58) Field of Classification Search
None
See application file for complete search history.

(56) References Cited

U.S. PATENT DOCUMENTS

| | | |
|---|---|---|
| 5,976,526 A | 11/1999 | Atala |
| 2007/0224168 A1 | 9/2007 | Montarras et al. |
| 2007/0224173 A1 | 9/2007 | Koullick et al. |
| 2008/0311219 A1 | 12/2008 | Gosiewska et al. |
| 2009/0123412 A1* | 5/2009 | Healy ............ A61K 9/0019 424/78.17 |
| 2010/0331980 A1 | 12/2010 | Lee et al. |

FOREIGN PATENT DOCUMENTS

CN    102140438 A    8/2011

OTHER PUBLICATIONS

Léobon et al. "Myoblasts transplanted into rat infarcted myocardium are functionally isolated from their host." Proceedings of the National Academy of Sciences 100.13 (2003): 7808-7811.*
Kovanen, Vuokko. "Intramuscular extracellular matrix: complex environment of muscle cells." Exercise and sport sciences reviews 30.1 (2002): 20-25.*
Bierinx et al., "Mouse sectioned muscle regenerates following autografting with muscle fragments: A new muscle precursor cells transfer?", Neuroscience Letters, Limerick, IE, vol. 431, No. 3, Jan. 4, 2008, pp. 211-214.
Bischoff et al., "A Satellite Cell Mitogen from Crushed Adult Muscle", Developmental Biology, Academic Press, Amsterdam, NL, vol. 115, No. 1, May 1, 1986, pp. 140-147.
Zammit P. et al., "Kinetics of Myoblast Proliferation Show That Resident Satellite Cells Are Competent to Fully Regenerate Skeletal Muscle Fibers", Experimental Cell Research, vol. 281, No. 1, Nov. 15, 2002, pp. 39-49.
Fan Y. et al., "A potential alternative strategy for myoblast transfer therapy: The use of sliced muscle grafts", Cell Transplantation, Cognizant Communication Corp, US, vol. 5, No. 3, May 1, 1996, pp. 421-429.
Montarras D. et al., "Direct Isolation of Satellite Cells for Skeletal Muscle Regeneration", Science, American Assoication for the Advancement of Science, US, vol. 309, Sep. 23, 2005, pp. 2064-2067.
Lawson-Smith M J et al., "The identification of myogenic cells in skeletal muscle, with emphasis on the use of tritiated thymidine autoradiography and desmin antibodies", Journal of Anatomy, vol. 192, Feb. 1998, pp. 161-171.

(Continued)

*Primary Examiner* — Robert Yamasaki
(74) *Attorney, Agent, or Firm* — Thomas J. Engellenner; Reza Mollaaghababa; Pepper Hamilton LLP

(57) ABSTRACT

The invention is directed to methods and compositions for obtaining uniform sized muscle fiber fragments for transplantation. These muscle fiber fragments are able to reconstitute into long fibers that are oriented along native muscle. The implanted muscle cells integrate with native vascular and neural network, as confirmed by histology and immunohistochemistry. This invention is particularly advantageous because autologous muscle can be harvested from a donor site, processed and injected into target sites in the operating room. The fragmented muscle fibers can be readily integrated within the host.

13 Claims, 8 Drawing Sheets

(56) References Cited

OTHER PUBLICATIONS

Supplementary European Search Report issued Mar. 18, 2015 corresponding to European Application No. 12823362.4 (10 sheets).
Labarge et al. "Biological Progression from Adult Bone Marrow to Mononucleate Muscle Stem Cell to Multinucleate Muscle Fiber in Response to Injury", Cell. Nov. 15, 2001, vol. 111, No. 4, pp. 589-604; p. 589, para 2-3; p. 590, para 2; p. 594, para 3; p. 599, para 2 (2002).
Burden "Guide to the Homogenization of Biological Samples", Random Primers, No. 7, pp. 1-14; abstract; p. 11, para 3 (2008).
International Search Report, PCT/US2012/050879, mailed Jan. 18, 2013 (9 pages).

* cited by examiner

MUSCLE TISSUE REGENERATION USING MUSCLE FIBER FRAGMENTS

GOVERNMENT RIGHTS

This invention was made with Government support under Grant No. W81XWH-08-1-0333, awarded by the Department of Defense—Orthopedics Trauma Research Program (OTRP). The Government has certain rights in this invention.

BACKGROUND OF THE INVENTION

The technical field of this invention relates to methods and compositions for the regeneration of muscle tissue. The invention also relates to constructs containing muscle tissue.

Reconstruction of skeletal muscle tissue lost by traumatic injury, tumor excision or ablation, or functional damage is hindered by the lack of available functional muscle tissue or muscle tissue substitutes. Autografts have been used clinically but require the presence of sufficient donor muscle tissue nearby and can leave muscle defects at the donor site. Herter et al., (J. Plast Reconstr. Aesthetic Surgery 60, 760-768 (2007)) provides an analysis of the various locations providing donor tissue and the benefits and disadvantages of these techniques.

Current methods for muscle regeneration without grafts rely primarily on muscle cell or fiber isolation and expansion through tissue culture in vitro. These cells or fibers are used for either injection therapy or engineering muscle tissue using scaffolds to achieve muscle function. These processes require cell manipulation and lengthy time before they can be used for therapy. Additionally, when the cells or long fibers are injected directly into the muscle, the method is limited by the difficulty in controlling orientation of cells or fibers and low survivability due to delay in vascular and neural integration. Thus, there exists a need for better methods for regenerating muscle in regions in need of repair, either via injection or implantation, so that the transplant can integrate readily with host vascular and neural networks and produce viable muscle.

SUMMARY OF THE INVENTION

Methods and compositions are disclosed for muscle regeneration. It has been discovered that disaggregated muscle fiber fragments are particularly effective in regeneration of functional muscle tissue. In some preferred embodiments, the fragments retain functional satellite cells but exhibit cell wall rupture and have an average size of less than 150 µm. The methods include the preparation and implantation of compositions by extracting muscle tissue from a donor site, disaggregating muscle fibers from the extracted tissue, and fragmenting disaggregated muscle fibers into fiber fragments that exhibit cell wall rupture and preferably have an average size of less than 150 µm, while retaining functional satellite cells. Upon implantation, the muscle fiber fragment compositions are capable of reconstituting or reconstructing elongated muscle fibers from the fragments and orienting in alignment with native muscle fibers when implanted in target muscle site.

In one aspect of the invention the cell fragments have an average size of less than 300 µm, preferably less than 150 µm, and in some instances more preferably between about 80 µm and 120 µm or between about 90 µm and 110 µm. The fragments can take any shape but preferably are rounded or oblong, e.g., with an aspect ratio of the long-to-short dimensions being between about 2:1 and 1:1. Since myofibers are long, cylindrical, multinucleated cells, it can also be preferable that the fragments retain at least one nucleus as well as be associated with at least one functional satellite cell.

In one embodiment the step of extracting muscle tissue can be practiced by extracting autologous muscle tissue and the step of disaggregating muscle fibers from tissue further comprises disaggregating the muscle fibers with an enzyme, such as Collagenase type I. The step of fragmenting the individual fibers into fragments can be practiced by mechanical agitation, e.g., via fluid transfer (pipetting) or via sonication. In some instances, fragmentation can be conducted until at least about 75% of the myofiber fragments exhibit cell wall rupture.

The therapeutic use of the invention can be practiced by delivering the composition to the muscle defect target site. In one approach, the composition can be suspended in a physiologically compatible fluid and injecting the composition into the muscle defect target site. Alternatively, the composition can be seeded onto a scaffold and the seeded scaffold implanted at a muscle defect target site.

The method can further include the step of co-administering the composition with an adjuvant, such as stem cells, muscle progenitor cells, growth factors or combinations of such agents. For example, the adjuvant can include at least one growth factor selected from the group of bone morphogenic protein (BMP), a RUNX-2 protein, a LIM mineralization protein, a fibroblast growth factor, a platelet derived growth factor, an epidermal growth factor, an insulin-like growth factor, a transforming growth factor-α, a transforming growth factor-β, a nerve growth factor (NGF), a brain-derived neurotrophic factor (BDNF), neuregulin (NRG), and agrin.

When a scaffold is used it can be preferably to culture the scaffold-supported fragments in vitro before delivering the scaffold to muscle defect target site. The scaffold can be an injectable scaffold selected from collagen gel, fibrin gel, alginate gel, or UV-induced crosslinkable gel system. Alternatively, the scaffold can be an implantable scaffold comprising an organic or polymeric matrix. The organic matrix can be, for example, decellularized tissue, such as submuscosa. Examples of polymeric matrix materials can be one or more natural polymers, e.g., collagen or elastin, or one or more synthetic polymer such as polycaprolactone (PCL), poly(D, L-lactide-co-glycolide) (PLGA), polylactide (PLA), poly (lactide-co-captrolactone) (PLCL), or combinations thereof.

In some embodiments, the matrix can be an electrospun fiber matrix formed by a combination of at least one natural polymer and at least one synthetic polymer, e.g., collagen and polycaprolactone (PCL). The seeded scaffold can further include a bone morphogenic protein (BMP), a RUNX-2 protein, a LIM mineralization protein, a fibroblast growth factor, a platelet derived growth factor, an epidermal growth factor, an insulin-like growth factor, a transforming growth factor-α, a transforming growth factor-β, or a combination thereof.

This invention describes uniformly structured small fragments of muscle fiber for efficient functional muscle regeneration as well as methods of making and using these muscle fiber fragments. The use of small muscle fiber fragments induces efficient re-assembly of injected fragments into host muscle tissue along the fiber direction of native muscle. Integration into host's vascular and neural network has been observed.

BRIEF DESCRIPTION OF THE DRAWINGS

FIG. 6A is a schematic diagram of implantation of MF/collagen construct into surgically induced TA muscle defect in rats. Implantation of MF/collagen into the defected TA muscle efficiently induced enhanced muscle restoration functionally [FIG. 6B] and structurally (FIG. 6C, 4 wks after implantation), *ANOVA and Tukey analysis in B and C, P<0.05, n=7, two independent experiments;

FIG. 7A is a schematic diagram of MF injection into urinary sphincter injury;

FIG. 7B is a graph showing enhanced urodynamic function due to improved sphincter function after MF injection. The urine leak point pressure with (P2) and without (P1) electrical stimulation. P2−P1=maximal bladder pressure that external sphincter sustain, *Student t-test, P<0.01, n=3;

DETAILED DESCRIPTION

Figure 1:
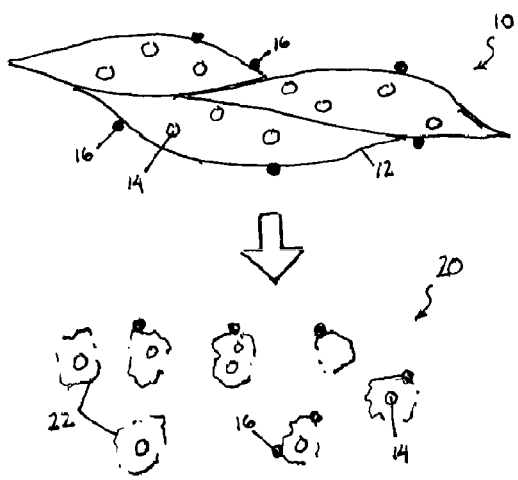
FIG. 1 is a schematic illustration of a method of forming muscle fiber fragments from a myofiber cell for regeneration of muscle tissue according to the invention.

So that the invention may more readily be understood, certain terms are first defined:

The term "about" or "approximately" means within an acceptable error range for the particular value as determined by one of ordinary skill in the art, which will depend in part on how the value is measured or determined—e.g., the limitations of the measurement system, or the degree of precision required for a particular purpose. For example, "about" can mean within 1 or more than 1 standard deviations, as per the practice in the art. Alternatively, "about" can mean a range of up to 20%, preferably up to 10%, more preferably up to 5%, and more preferably still up to 1% of a given value. Where particular values are described in the application and claims, unless otherwise stated, the term "about" meaning within an acceptable error range for the particular value should be assumed.

As used herein and in the appended claims, the singular forms "a," "an," and "the," include plural referents unless the context clearly indicates otherwise. Thus, for example, reference to "a molecule" includes one or more of such molecules, "a resin" includes one or more of such different resins and reference to "the method" includes reference to equivalent steps and methods known to those of ordinary skill in the art that could be modified or substituted for the methods described herein.

"Anisotropic" means that the physical properties (e.g., elasticity, tensile strength, elongation at break, etc.) of a material (e.g., myotube, scaffold, etc.) are different depending upon the direction of action (e.g., stretch or strain), as opposed to "isotropic," in which the properties of a material are identical in all directions. For example, an anisotropic cell substrate may have a greater ultimate tensile strength along one axis (e.g., the longitudinal axis) than along an axis perpendicular to the axis (e.g., by 0, 1 or 2 to 4, 5, 6 or more MPa). The elongation at break may be smaller along one axis (e.g., the longitudinal axis) than along an axis perpendicular to the axis (e.g., by 10, 20, 30 or 40 to 50, 60, 70 or 80% or more). The peak of a stress curve (MPa) may be reached at a lower strain (%) along one axis (e.g., the longitudinal axis) as compared to an axis perpendicular to the axis. Preferably, the material is tested under wet condition (e.g., immersed in phosphate buffer saline) at room temperature.

The term "attach" or "attaches" as used herein refers to cells that adhere directly or indirectly to a substrate as well as to cells that adhere to other cells.

The phrase "biocompatible substrate" as used herein refers to a material that is suitable for implantation into a subject onto which a cell population can be deposited. A biocompatible substrate does not cause toxic or injurious effects once implanted in the subject. In one embodiment, the biocompatible substrate is a polymer with a surface that can be shaped into the desired structure that requires repairing or replacing. The polymer can also be shaped into a part of a structure that requires repairing or replacing. The biocompatible substrate provides the supportive framework that allows cells to attach to it, and grow on it. Cultured populations of cells can then be grown on the biocompatible substrate, which provides the appropriate interstitial distances required for cell-cell interaction.

A "biodegradable scaffold," "biodegradable mesh" or "biodegradable matrix" is a scaffold having materials capable of being degraded and/or absorbed in a subject's body. Desirably, the scaffold or matrix is porous to allow for cell deposition both on and in the pores of the matrix, and in certain embodiments, is shaped. Such formulations can be prepared by supplying at least one cell population to a biodegradable scaffold to seed the cell population on and/or into the scaffold. In some embodiments, the seeded scaffold is then implanted in the body of the recipient subject, where the organized cell populations facilitate the formation of functional tissue structures.

The term "co-polymer" as used herein is intended to encompass co-polymers, ter-polymers, and higher order multiple polymer compositions formed by block, graph or random combination of polymeric components.

The term "decellularized" or "decellularization" as used herein refers to a biostructure (e.g., an organ, or part of an organ), from which the cellular and tissue content has been removed leaving behind an intact acellular infra-structure. Organs such as the kidney are composed of various specialized tissues. The specialized tissue structures of an organ, or parenchyma, provide the specific function associated with the organ. The supporting fibrous network of the organ is the stroma. Most organs have a stromal framework composed of unspecialized connecting tissue which supports the specialized tissue. The process of decellularization removes the specialized tissue, leaving behind the complex three-dimensional network of connective tissue. The connective tissue infra-structure is primarily composed of collagen. The decellularized structure provides a biocompatible substrate onto which different cell populations can be infused. Decellularized biostructures can be rigid, or semi-rigid, having an ability to alter their shapes. Examples of decellularized organs useful in the present invention include, but are not limited to, the heart, kidney, liver, pancreas, spleen, bladder, ureter and urethra.

The term "diameter" as used herein in respect to the muscle fiber fragments means the average diameter of the fragments. Preferably, at least 80% of all fragments are within the stated diameter range. More preferably, at least 90% of all fragments are within the stated diameter range, and most preferably, at least 95% of all fragments are within the stated diameter range.

The terms "electrospinning" or "electrospun," as used herein refers to any method where materials are streamed, sprayed, sputtered, dripped, or otherwise transported in the presence of an electric field. The electrospun material can be deposited from the direction of a charged container towards a grounded target, or from a grounded container in the direction of a charged target. In particular, the term "electrospinning" means a process in which fibers are formed from a charged solution comprising at least one natural biological material, at least one synthetic polymer material, or a combination thereof by streaming the electrically charged solution through an opening or orifice towards a grounded target.

The term "elongated" means that, for example, the muscle fiber has a greater length than width. Preferably, an elongated muscle fiber will have a length of at least 5 times the width, or more preferably at least 10 times the width, at least 50 times the width, or at least 100 times the width.

"Express" or "expression" of a protein or other biological marker means that a gene encoding the same of a precursor thereof is transcribed, and preferably, translated. Typically, according to the present invention, expression of a coding region of a gene will result in production of the encoded polypeptide, such that the cell is "positive" for that protein or other biological marker.

"Fibroblasts" are cells that synthesizes the extracellular matrix and collagen and are found in connective tissue throughout the body "Implant" refers to a product configured to repair, augment or replace (at least a portion of) a natural tissue of a subject (e.g., for veterinary or medical (human) applications). The term "implantable" means the device can be inserted, embedded, grafted or otherwise chronically attached or placed on or in a patient. Implants include, but are not limited to, a scaffold or bioscaffold (which may or may not further comprise cells seeded onto the scaffold or bioscaffold).

"Isolated" as used herein signifies that the cells are placed into conditions other than their natural environment. Tissue or cells are "harvested" when initially isolated from a subject, e.g., a primary explant.

The term "muscle defect" as used herein is intended to broadly encompass disorders, diseases, defects and injuries that can impair muscle function including but not limited to physical injuries, burns, surgical tissue excisions, muscle wasting, muscular dystrophy, infarcts, ischemic events and neuromuscular disorders.

Muscle cells include, but are not limited to, muscle fibers or myocytes, and may be of any suitable species, and in some embodiments are of the same species as the subject into which tissues are implanted. Mammalian cells (including mouse, rat, dog, cat, monkey and human cells) are in some embodiments particularly preferred. Muscle cells include skeletal muscle cells, smooth muscle cells and cardiac muscle cells.

The muscle fiber fragments may be syngeneic (i.e., genetically identical or closely related, so as to minimize tissue transplant rejection), allogeneic (i.e., from a non-genetically identical member of the same species) or xenogeneic (i.e., from a member of a different species). Syngeneic muscle fiber fragments include those that are autologous (i.e., from the patient to be treated) and isogeneic (i.e., a genetically identical but different subject, e.g., from an identical twin). Muscle fibers fragment may be obtained from, e.g., a donor (either living or cadaveric) or derived from cells in an established cell strain or cell line. For example, muscle fiber fragments may be harvested from a donor (e.g., a potential recipient of a bioscaffold graft) using standard biopsy techniques known in the art. In one preferred embodiment, the muscle fiber fragments are autologous.

A muscle fiber (or "myofiber") is a multinucleated single muscle cell. Physically, they are highly elongated and range in size from a under a hundred microns in diameter and a few millimeters in length to a hundreds of microns across and a few centimeters in length. The cell is densely packed with contractile proteins, energy stores and signaling mechanisms.

Muscle fiber cells are formed from the fusion of developmental myoblasts (a type of embryonic progenitor cell that gives rise to a muscle cell). The myofibers are long, cylindrical, multinucleated cells composed of actin and myosin myofibrils repeated as a sarcomere, the basic functional unit of the muscle fiber and responsible for skeletal muscle's striated appearance and forming the basic machinery necessary for muscle contraction.

The muscle fiber is the smallest complete contractile system. As such, it requires subsystems for metabolism, excitation and contraction. For effective force production, contraction must be excited along the whole length of a fiber simultaneously. The contraction signal is spread rapidly along the fiber by means of the T-tubule system, which signals the rapid release of calcium ions from the sarcoplasmic reticuluum (SR). As soon as the contraction signal ends, ATP-driven calcium pumps begin sequestering almost all the intracellular calcium in this SR.

Within each myofiber is a network of myofibrils. These fibrils contain the proteins that do the actual force production. It is because of these fibrils that skeletal muscle demonstrates its characteristic striated pattern. An extensive network of proteins binds each myofibril to its neighboring fibril and to the cell membrane.

"Myoblasts" are a type of muscle stem cell, and are normally closely associated with myofibers during the course of their life cycle in the vertebrate organism. If the myofiber is injured, the myoblasts are capable of dividing and repopulating it. Typically, after muscle injuries myofibers become necrotic and are removed by macrophages (Hurme et al. (1991) Healing of skeletal muscle injury: an ultrastructural and immunohistochemical study, *Med. Sci Sports Exerc.* 23, 801-810). This induces proliferation and fusion of myoblasts to form multinucleated and elongated myotubes, which self-assemble to form a more organized structure, namely muscle fibers (Campion (1984) The muscle satellite cell: a review, *Int. Rev. Cytol.* 87, 225-251).

"Myocytes" are muscle cells, muscle fibers, or skeletal muscle cells. Myocytes are formed by when myoblasts fuse together.

As noted above, "myofibrils" are the slender threads of a muscle fiber composed of numerous myofilaments. Myofibrils run from one end of the cell to the other and attach to the cell surface membrane at each end.

"Myotubes" are elongated, multinucleated cells, normally formed by the fusion of myoblasts. Myotubes can develop into mature muscle fibers, which have peripherally-located nuclei and myofibrils in their cytoplasm (e.g., in mammals). Under low serum conditions, myoblasts exit the cells cycle and fuse to form multinucleated myotubes, which become contractile.

The terms "nanoparticles," "nanostructures," and "quantum dots" are used interchangeably herein to describe materials having dimensions of the order of one or a few nanometers to a few micrometers, more preferably from about 1 to about 1000 nanometers.

The term "natural biostructure" as used herein refers to a biological arrangement found within a subject, for example, organs, that include but are not limited to heart, kidney, liver, pancreas, spleen, bladder, ureter and urethra. The term "natural biostructure" is also intended to include parts of biostructures, for example parts of organs, for example, the renal artery of a kidney. A natural biological material can be a naturally occurring organic material including any material naturally found in the body of a mammal, plant, or other organism. A synthetic polymer material can be any material prepared through a method of artificial synthesis, processing, or manufacture. Preferably the synthetic material is a biologically compatible material. The natural or synthetic materials are also those that are capable of being charged under an electric field.

"Oriented" cells and/or cell substrates typically have one (or more) axis of orientation (e.g., longitudinal axis), which may be in any desired direction within the region of interest. It will be appreciated that "orienting" as used herein may include partial or total orientation, so long as a sufficient increase in organization is achieved to produce the effect or benefit intended for the particular implementation of the method described herein. For example, fibers and/or cells may be oriented along a longitudinal axis such that greater than 70, 80, 90, or 95% or more of the fibers and/or cells are at an angle of 50, 40, 30, 20, or 10 degrees or less from the reference axis in any direction.

As used herein, the term "patient" refers to a host animal that is in need of repair or reconstruction of muscle tissue lost by traumatic injury, tumor ablation, or functional damage, etc. Preferred patients are mammals. Examples of patients include but are not limited to, humans, horses, monkeys, dogs, cats, mice, rates, cows, pigs, goats and sheep. In some embodiments, "patients" are generally human patients.

The "primary culture" is the first culture to become established after seeding disaggregated cells or primary explants into a culture vessel. "Expanding" or "expansion" as used herein refers to an increase in number of viable cells. Expanding may be accomplished by, e.g., "growing" the cells through one or more cell cycles, wherein at least a portion of the cells divide to produce additional cells. "Growing" as used herein includes the culture of cells such that the cells remain viable, and may or may not include expansion and/or differentiation of the cells.

"Satellite cells," as used herein, are small mononuclear progenitor cells with little cytoplasm found in mature muscle. They are located between the basement membrane and sarcolemma (cell membrane) of individual muscle myofibers. Satellite cells are able to differentiate and fuse to augment existing muscle fibers and to form new myofibers. In undamaged muscle, the majority of satellite cells are quiescent; they neither differentiate nor undergo cell division. In response to mechanical strain, satellite cells become activated. Activated satellite cells initially proliferate as skeletal myoblasts and can and differentiate into myotubes before undergoing myogenic differentiation. In one embodiment of the present invention, the donor muscle fiber contains satellite cells. In some embodiments, a muscle fiber fragment will contain, on average, 2-3 satellite cells. In other embodiments, the muscle fiber fragments will contain more satellite cells.

"Scaffold" refers to an array of natural or synthetic matrix molecules to which cells or fibers can attach. The fibers may include extracellular matrix molecules or components, such as elastin, elastic strands or peptides, fibrin, collagen, proteoglycans, hyaluronan or hyaluronan oligomers, synthetic fibers or fibrils, or bioactive hydrogels, microparticles, beads, liposomes, or vesicles. Scaffolds may further include extracellular matrix components, such as elastin, elastin-like or elastin-mimetic peptides, fibrin, proteoglycans, commercially available matrix or matrix-substitutes such as Matrigel™ matrix (BD Biosciences, San Jose, Calif., USA), collagen of any type, synthetic fibers or fibrils, or bioactive hydrogels. In some embodiments, a scaffold as described in U.S. Pat. Pub. 2010/0331980 and herein incorporated by reference in its entirety is use. In some embodiments, the scaffold is an electrospun scaffold which exhibits significant uniaxial mechanical properties, which are reflective of an extremely oriented underlying extracellular matrix. In some embodiments, the scaffold includes an electrospun nanofiber mesh. In some embodiments, the mesh has a uniaxial fiber angle.

The term "size" as used herein in respect to the muscle fiber fragments means the length of the fragments along their average diameter.

The terms "rupture" and "disruption" as well as derivatives thereof, as used herein, characterize a breach or fault in the cell membrane that exposes at least a portion of a cell's cytoplasm to the extracellular environment.

The term "substantially," as used herein, means over 50%, or more preferably at least 75%, or more preferably at least 85%, or more preferably at least 90%, or even more preferably at least 95%. The phrase "substantial cell wall rupture" means that the cell wall is ruptured or disrupted in over 50% of the cells in the sample. More preferably, at least 75%, at least 85%, at least 90%, or at least 95% of the cell walls are ruptured.

As used herein, the phrase "target muscle site" is the location that is in need of repair or reconstruction of muscle tissue. The target muscle site may be a smooth muscle, cardiac muscle, skeletal muscle or combinations thereof. The target muscle site may be a site of traumatic injury, tumor ablation, or functional damage, etc. Alternatively, the target muscle site may be a site of ageing muscle or dystrophic muscle.

The phrase "three-dimensional scaffold" as used herein refers synthetic or largely acellular organic matrices suitable for cell seeding and growth. In certain preferred embodiments, "three-dimensional scaffold" refers to the residual infra-structure formed when a natural biostructure, e.g. an organ or tissue, is decellularized. This complex, three-dimensional, scaffold can provide a highly supportive framework that allows cells to attach to it, and grow on it. Cultured populations of cells can then be grown on the three-dimensional scaffold, which provides the exact interstitial distances required for cell-cell interaction. This provides a reconstructed organ that resembles the native in vivo organ or tissue.

Such three-dimensional scaffolds can be perfused with a population of cultured cells, e.g., muscle cells. In some embodiments, the scaffolds can also be seeded with other cell types, such as endothelial cells, which grow and develop to provide an endothelial tissue layer capable of supporting growth and development of at least one additional cultured cell population, e.g., muscle cells.

"Treat" refers to any type of treatment that imparts a benefit to a subject, e.g., a patient afflicted with or at risk for developing a disease (e.g., a musculoskeletal disease). Treating includes actions taken and actions refrained from being taken for the purpose of improving the condition of the patient (e.g., the relief of one or more symptoms), delay in the onset or progression of the disease, etc. In some embodiments, treating includes reconstructing skeletal muscle tissue (e.g., where such tissue has been damaged or lost by, e.g., injury or disease) by implanting an anisotropic scaffold (with or without muscle cells) into a subject in need thereof. Scaffolds may be implanted, e.g., at or adjacent to the site of injury, and/or at another site in the body of a subject that would impart a benefit to the subject, as would be appreciated by one of skill in the art.

Without being limited to any particular theory, it is believed that implantation of muscle cell fragments induces a cascade of events that rapidly lead to the production of new muscle tissue. These events may include self-directed repair of the fragments and/or growth into new muscle cells or the activation of quiescent satellite cells, which repair the fragments and/or induce growth of new muscle cells. Moreover the fragments themselves appear to provide a ready source of actin and myosin myofibrils that can be scavenged and used to reconstitute and repair other fragments and/or accelerate the growth of new muscle cells.

METHODS AND COMPOSITIONS

FIG. 1 is a schematic illustration of a method of forming muscle fiber fragments from a long myofibers for regeneration of muscle tissue. At the top of the figure, an intact, elongated muscle fiber cell 10 is shown schematically having a cell wall 12, multiple nuclei 14 and associated satellite cells 16. At the bottom of the figure, following treatment according to the invention, a set of fragments 20 are shown. The fragments are characterized by disrupted cell walls 22. Preferably most fragments retain at least one native nucleus and at least one associated satellite cell 16.

Figure 2:
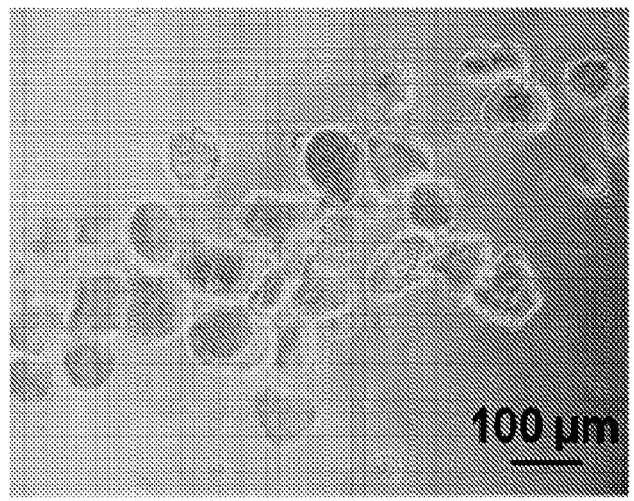
FIG. 2 is a microphotograph of muscle fiber fragments according to the invention.

FIG. 2 is a microphotograph of muscle fiber fragments formed according to the invention. Most of the fragments are on the order of 100 μm in size. While not necessarily visible at this magnification, these fragments, exhibit disrupted cell walls. Despite disruption satellite cells remain associated with the fragments.

Figure 3:
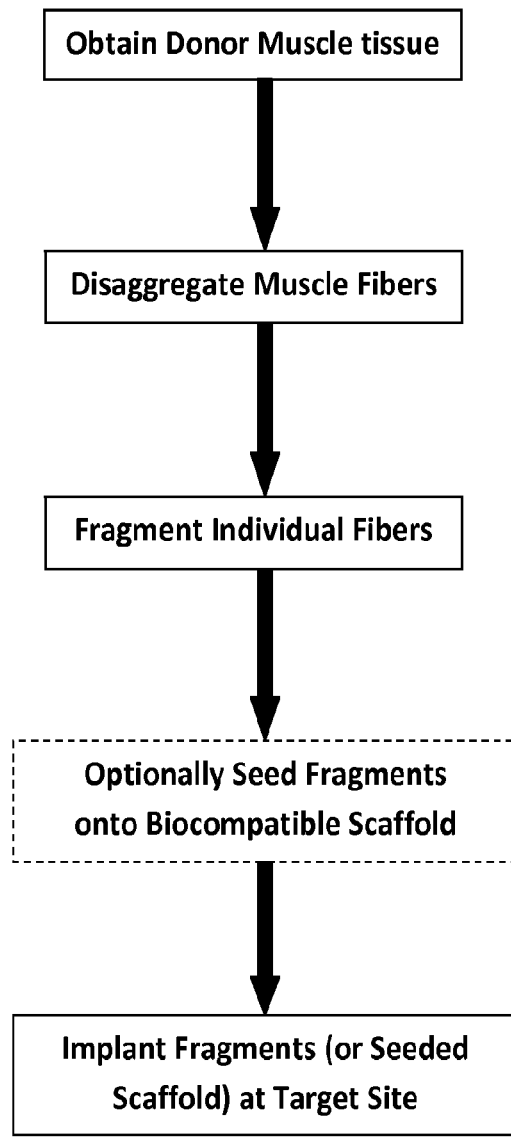
FIG. 3 is block diagram of steps in muscle tissue regeneration according to the invention.

FIG. 3 is block diagram of steps in muscle tissue regeneration according to the invention. In the first step, donor muscle tissue is obtained, e.g., by excision or extraction. In the next step, the tissue is disaggregated into individual fibers, e.g., by mincing and/or enzymatic digestion of connective tissue to free the fibers from each other. In the next step, the individual fibers are fragmented, e.g., by mechanical agitation and/or filtration. Optionally the fiber fragments can be seeded onto scaffolds. (For further details of this technique, see for example, U.S. Patent Application Pub. No. US 2010/0331980 by Lee et al., which is herein incorporated by reference.) Finally, the fragments or seeded matrices) can be injected or implanted at a target site where muscle tissue regeneration is desired. More details as to methods and compositions are provided in the following sections.

I. Fiber Preparation

It has been surprisingly found that, by transplanting uniformly sized muscle fiber fragments of less than about 150 μm at a muscle defect site, the fragments can provide building blocks for the production of viable muscle tissue and facilitate the integration of such tissue into the host vascular and neural network. Thus, the methods as provided herein enable the use of autologous cell populations derived from the subject's own tissue to be efficiently and quickly prepared.

The use of small muscle fiber fragments induces efficient re-assembly of injected fragments (or fragments on a scaffold) into host muscle tissue along the fiber direction of native muscle. These fiber fragments can then integrate into the host vascular and neural network.

To prepare the uniform muscle fiber fragments, muscle tissue is first extracted from a donor site. This muscle tissue should contain viable muscle cells, as well as satellite cells. Myofiber fragments are then obtained by the enzymatic digestion, mechanical fragmentation and filtration. The muscle fiber fragments thus obtained can be, for example, directly injected into a target site, formed into particles/powders and then injected into the target site or applied to a scaffold that is cultured and then implanted at a target site.

The muscle tissue may be extracted from a donor site by any known technique. The donor muscle tissue may be syngeneic (autologous or isogeneic), allogeneic, or xenogeneic. In one embodiment, the donor muscle tissue is autologous muscle tissue. This is particularly advantageous since autologous tissue is not rejected by the immune system. Muscle tissue can be extracted, for example, from a limb muscle such as the quadriceps, or from another appropriate muscle (e.g., a hind leg muscle of an animal) using standard biopsy techniques known in the art.

Mincing the muscle tissue provides small sized pieces for disaggregation. Preferably, the muscle fibers are minced to a small size. In some embodiments, the muscle tissue can be minced with sterile forceps and/or scissors to a size of less than 5 mm, 4, mm, 3 mm, 2 mm, 1 mm, or 0.5 mm (The size distribution can also be inhomogenous).

After mincing, the muscle fiber is preferably disaggregated with a disaggregation agent. The disaggregation agent preferably should digest the muscle fiber but not dissociate the satellite cells from the myocyte. In one embodiment, the disaggregation agent is an enzyme and the muscle fiber is digested. One preferred enzyme is Collagenase type I. Other disaggregation agents that may be use include, but are not limited to other collagenases, trypsin, lipase, hyaluronidase, deoxyribonuclease, Liberase HI, and pepsin, or mixtures thereof.

The disaggregated muscle fiber is then fragmented. In one embodiment, the digested muscle fiber is mechanically fragmented. One preferred method of mechanically fragmenting the muscle fiber is via mixing, such as by repeated pipetting. Repeated uptake into a pipette tip and release will cause the muscle fibers to mix and fragment. In one embodiment, the digested muscle fiber fragment is taken into a pipette tip and released at least 5, 10, 15, 20, 25, 30, or more times. Another method of mechanically fragmenting the muscle fiber is through vigorous stirring. Yet another method of mechanically fragmenting the muscle fiber is via sonication at a frequency and power to prevent substantial lysing of the satellite cells.

The solution containing the fragmented muscle fibers is then filtered to a diameter of less than 150 μm. The inventors have found that a preferable filter size is less than 150 μm. In one embodiment, fiber fragments are less than 140 μm, 130 μm, 120 μm, 110 μm, or 100 μm in diameter. In other embodiments, the fiber fragments are between 40 and 150 μm, 50 and 140 μm, 60 and 130 μm, 70 and 120 μm, 80 and 110 μm or 90 and 100 μm. In other embodiments, the fiber fragments are between 60 and 150 μm, 60 and 140 μm, 70 and 130 μm, 80 and 120 μm, 80 and 110 μm or 80 and 100 μm. In one embodiment, fiber fragments between 80 and 100 μm in diameter have been shown to be particularly useful as uniform fiber fragments for implantation and generation of muscle tissue. In one embodiment, the filter is a 100-μm filter. Optionally, the smaller sized fragments may be removed from the muscle fiber by screening through a small filter (i.e., an 80, 70, 60, 50, 40, or 30 μm filter) and discarding the filtrate. The terms filter and strainer are used interchangeably herein.

The uniform myofiber fragments obtained by the methods as described herein contain at least two components. They contain functional satellite cells and myofiber cellular fragments. In one embodiment, at least 50% of the satellite cells are functional. In another embodiment, at least 75%, at least 85%, at least 90%, or at least 95% of the satellite cells are functional. The myofibers in the uniform myofibers fragments have substantial cell wall rupture. The cell wall is ruptured in over 50%, at least 75%, at least 85%, at least 90%, or at least 95% of the myofibers. The functionality of the satellite cells in the uniform myofibers fragment can be measured by any method as known in the art. For example, the satellite cells may be fluorescently labeled with a dye such as Vybrant, GFP (Green Fluorescent Protein), or Pax7 immunostaining.

The amount of muscle satellite cells in the uniform myofiber fragments is an effective amount, i.e., the myofibers fragments contain sufficient satellite cells to allow the cells to perform their myogenesis role. The exact amount of satellite cells within the fiber fragment will vary according to factors such as the type of donor material, the type of muscle damage being repaired, the mode of administration, and the additional components provided in the fiber fragment.

In one embodiment, the muscle fiber fragments may be acellular muscle fiber fragments. In another embodiment, the muscle fiber fragments may be acellular muscle fiber-derived particles/powders. The use of acellular fragments without immunogenic components can be a promising approach to allogeneic transplantation for functional muscle regeneration. By removing immunogenic components such as cells and residual DNA, acellular fragments can reduce immune responses when compared to donor cells-contained muscle fibers. In addition, acellular fragments play significant roles such as, i) a muscle specific template which can provide appropriate structural architecture and extracellular matrix for endogenous satellite cells adhesion, survival, and proliferation and ii) stimulation of muscle cells by secreting trophic factors.

II. Three-Dimensional Reconstructs

In some embodiments, the uniform fiber fragments are implanted at a muscle injury using scaffold, or a three-dimensional (3-D) reconstructs of engineered muscle tissue. The use of a 3-D reconstruct is particularly useful where the muscle injury contains large defect sites. 3-D muscle tissues can be prepared by combining muscle fibers fragments with scaffold systems such as injectable scaffolds (collagen gel, fibrin gel, alginate gel, or UV-induced cross-linkable gel system) or implantable scaffolds derived natural and synthetic polymers.

In one embodiment, the scaffold is formed using electrospinning to create a matrix. Electrospun matrices that are particularly useful are described, for example, in U.S. Pat. No. 7,531,503 "Cell Scaffold Matrices with Incorporated Therapeutic Agents," U.S. Pat. Pub. No. 2010/0129450 "Electrospun Cell Matrices," and U.S. Pat. Pub. No. 2010/0331980 "Aligned Scaffolding System for Skeletal Muscle Regeneration," each of which are incorporated by reference in their entirety.

The matrix onto which the uniform fiber fragments may be implanted are biocompatible and are preferably biodegradable. Representative materials for forming the biodegradable material include natural or synthetic polymers, such as, collagen, poly(alpha esters) such as poly(lactate acid), poly(glycolic acid), polyorthoesters and polyanhydrides and their copolymers, which degraded by hydrolysis at a controlled rate and are reabsorbed. These materials provide the maximum control of degradability, manageability, size and configuration. Preferred biodegradable polymer materials include polyglycolic acid and polyglactin, developed as absorbable synthetic suture material.

In one aspect of the invention, matrix is an electrospun matrices comprise at least one natural biological material component and at least one synthetic polymer material. In one embodiment, the natural biological material component comprises collagen (which can be derived from biological tissue sources or synthesized) and the synthetic polymer component can a high molecular weight polymer, e.g., having a molecular weight of at least 1000, preferably between 2,000 and 20,000. The natural component makes the matrices highly biocompatible and/or less immunogenic while the molecular weight polymer component can impart additional mechanical strength to the matrix and/or improve ease of manufacture by increasing viscosity and spinning characteristics of the solution during electrospinning. The materials being used in the electrospun matrices are capable of being charged or capable of being transported in a charged solution.

The electrospun matrices can further comprise a second natural component chosen to impart elasticity. For example, the natural biological material component can comprise elastin (which again can be derived from biological tissue sources or synthesized). Following electrospinning, the matrix can also be crosslinked for increased stability and strength, using various known crosslinking methods.

Examples of naturally occurring materials that may be included in the electrospun matrix include, but are not limited to, amino acids, peptides, denatured peptides such as gelatin from denatured collagen, polypeptides, proteins, carbohydrates, lipids, nucleic acids, glycoproteins, lipoproteins, glycolipids, glycosaminoglycans, and proteoglycans. In a preferred embodiment, the materials compound is an extracellular matrix material, including but not limited to collagen, fibrin, elastin, laminin, fibronectin, hyaluronic acid, chondroitin 4-sulfate, chondroitin 6-sulfate, dermatan sulfate, heparin sulfate, heparin, and keratan sulfate, and proteoglycans. These materials may be isolated from humans or other animals or cells. A preferred natural compound is collagen. Examples of collagen include, but are not limited to collagen I, collagen II, collagen III, collagen IV, collagen V, collagen VI, collagen VII, collagen VIII, collagen IX, and collagen X. Another preferred natural compound is elastin. Elastin fibers are responsible for the elastic properties of several tissues. Elastin is found, for example, in skin, blood vessels, and tissues of the lung where it imparts strength, elasticity and flexibility.

Examples of synthetic polymers that may be included in the electrospun matrix include, but are not limited to one or more of poly(lactic acid) polymers, poly(glycolic acid) polymers, poly(lactide-co-glycolides) (PLGA), poly(urethanes), poly(siloxanes) or silicones, poly(ethylene), poly(vinyl pyrrolidone), poly(2-hydroxy ethyl methacrylate), poly(N-vinyl pyrrolidone), poly(methyl methacrylate), poly(vinyl alcohol) (PVA), poly(acrylic acid), poly(vinyl acetate), polyacrylamide, poly(ethylene-co-vinyl acetate), poly(ethylene glycol), poly(methacrylic acid), polylactic acid (PLA), polyglycolic acids (PGA), nylons, polyamides, polyanhydrides, poly(ethylene-co-vinyl alcohol) (EVOH), polycaprolactone, poly(vinyl acetate), polyvinylhydroxide, poly(ethylene oxide) (PEO), and polyorthoesters. In one embodiment, the synthetic polymer component is a poly(lactic acid) polymer or a poly(glycolic acid) polymer or a co-polymer thereof, such as poly(D,L-lactide-co-glycolide), with a molecular weight from about 1000 to about 20,000.

In one embodiment, the scaffold is formed using a synthetic polymer using one or more of a variety of solvents and porogens. In one embodiment, the scaffold is formed using molecular self assembly. In one preferred embodiment, a hydrogel scaffold is formed.

The methods and compositions of the invention can be used for localized delivery of the uniform fiber fragments. Additional therapeutic and/or biological agents may also be added to the matrix, and controlled release of such agents at the target site in a subject is envisioned. The functional additions can include image enhancing or contrast agents (e.g., gadolinium, or barium), or therapeutic or otherwise biological agents. In one embodiment, the therapeutic or biological agent can be coupled to a nanoparticle, e.g., a quantum dot structure, that is activated by applied energy, e.g., by irradiation with radiation of a wavelength or a range of wavelengths readily absorbed by the nanoparticle.

The 3-D reconstruct can be treated with additives or drugs prior to implantation (before or after the polymeric substrate is implanted with the uniform muscle fiber fragments), e.g., to promote the formation of new tissue after implantation. Thus, for example, growth factors, cytokines, extracellular matrix components, and other bioactive materials can be added to the substrate to promote graft healing and formation of new tissue. Such additives will in general be selected according to the tissue or organ being reconstructed or augmented, to ensure that appropriate new tissue is formed in the engrafted organ or tissue (for examples of such additives for use in promoting bone healing, see, e.g., Kicker-Head, C. A. Vet. Surg. 24 (5): 408-19 (1995)). For example, vascular endothelial growth factor (VEGF, see, e.g., U.S. Pat. No. 5,654,273 herein incorporated by reference) can be employed to promote the formation of new vascular tissue. Growth factors and other additives (e.g., epidermal growth factor (EGF), heparin-binding epidermal-like growth factor (HBGF), fibroblast growth factor (FGF), cytokines, genes, proteins, and the like), nerve growth factor (NGF), brain-derived neurotrophic factor (BDNF), neuregulin (NRG), and agrin can be added in amounts in excess of any amount of such growth factors (if any) which may be produced by the cells seeded on the substrate. Such additives are preferably provided in an amount sufficient to promote the formation of new tissue of a type appropriate to the tissue or organ, which is to be repaired or augmented (e.g., by causing or accelerating infiltration of host cells into the graft). Other useful additives include antibacterial agents such as antibiotics.

A matrix can be stored and used shortly before implantation by seeding it with the uniform myofibers fragments. Many electrospun matrices are dry once they are spun and can be storage in a dry or frozen state. Storage conditions will depend on the electrospun compounds used and whether a therapeutic agent is incorporated onto or into the matrix. In embodiments where a therapeutic agent is incorporated, the matrix can be stored at temperatures below 0° C., under vacuum, or in a lyophilized state. Other storage conditions can be used, for example, at room temperature, in darkness, in vacuum or under reduced pressure, under inert atmospheres, at refrigerator temperature, in aqueous or other liquid solutions, or in powdered form depending on the materials in and on the matrix.

The matrices may be sterilized through conventional means known to one of ordinary skill in the art such as radiation, and heat. The matrices can also be combined with bacteriostatic agents, such as thimerosal, to inhibit bacterial growth. In some embodiments, the compositions can be treated with chemicals, solutions, or processes that confer stability in storage and transport.

III. Transplantation

In the present invention, the uniform myofiber fragments are made to be injected into a patient. The fiber fragments maintain viability of cells that can be readily integrated within the host after transplantation. Thus, the fiber fragments are capable of reconstructing into long fibers and orienting along native muscle. The fiber fragments reassemble into host muscle fibers and integrate with vascular and neural system to provide functional reconstructed or repaired muscle.

It was found that the formation of the muscle fiber fragments as described herein preserves the neuromusclular junction and thus allows for nerves to connect with the muscle fiber fragments as they form muscle fibers in the host. The connection of nerves is required for muscles to contract. Thus, the preservation of the neuromuscular junction is an important aspect of one embodiment of the present invention.

In one embodiment, the uniform myofiber fragments are directly injected into a target muscle site of a patient. The small size and uniformity of the fiber fragments allows for the reconstruction of the fiber fragments in long fiber that orient along the native muscle.

In one embodiment, the uniform myofibers fragments are implanted or seeded into a matrix where a 3-D reconstruct is formed and implanted into a patient.

The present invention includes a process whereby muscle fiber is harvested from a donor site in a patient, uniform muscle fiber fragments are prepared, and the uniform muscle fiber fragments are injected into target site(s) in the patient within the course of a single day. Thus, the patient is not required to undergo multiple visits to the hospital or similar location since the harvesting and injection can be done within a short time frame. In one embodiment, the muscle fiber is harvested from a donor site in a patient, uniform muscle fiber fragments are prepared while the patient remains in the operating room, and the uniform muscle fiber fragments are injected into target sites in the operating room. In some embodiments, the time frame between harvesting and injection is less than 8 hours. In other embodiments, the time frame is less than 6 hours. In other embodiments, the time frame is less than 4 hours. In other embodiments, the time frame is less than 3 hours. In other embodiments, the time frame is less than 2 hours. In other embodiments, the time frame is less than 1 hour.

Other embodiments and used of the invention will be apparent to those skilled in the art from consideration of the specification and practice of the invention disclosed herein. All U.S. Patents and other references noted herein for whatever reason are specifically incorporated by reference. The specification and examples should be considered exemplary only with the true scope and spirit of the invention indicated by the following claims.

EXAMPLES

Example 1

Preparation of Muscle Fiber Fragments

Uniformly structured muscle fiber fragments were isolated from tibialis anterior (TA) and gastrocnemius (GN) muscles of C57BL6 mice (male, 10-12 weeks). Isolated TA or GN muscles were minced with two disposable scalpels. The muscle tissue was minced into quite small sizes. After mincing, the fragments were digested with 0.2% collagenase type I in serum free DMEM with shaking at 37° C. for 1 hr. After enzymatic digestion, myofibers were pipetted to dissociate into individual fragments. Subsequently, the myofibers solution was immediately filtered through a cell strainer (100 μm size, BD falcon) to obtain uniform sized myofiber fragments. Small myofiber fragments were labeled with Vybrant fluorescent dye (DiD, Invitrogen) for fiber tracking after implantation in animals. Confocal microscopy confirmed that isolated fiber fragments including cells on their surface were fluorescently labeled with Vybrant and the size of fiber fragments showed approximately 100 μm in a diameter.

Example 2

Transplant of Muscle Fiber Fragments

To determine whether the processed muscle fragments can be developed as an injection therapy, isolated muscle fiber fragments were injected to the gluteal region of C57BL6 mice (10-12 weeks). 10 μl of fiber fragments solution in PBS (500 in fiber fragment numbers/injection) were injected twice toward the incision site (0.5-1 cm) on the gluteal region with a hamilton syringe (26 G, 10 μl). After transplantation, the incision was closed by suture. At 1, 2, 3, and 4 weeks after transplantation, the muscle tissue with incision site was harvested and further frozen in OCT compounds.

To examine whether injected muscle fiber fragments would reassemble into host muscle fibers and integrate with vascular and neural system of host animal, histological and immunohistological studies were performed using the harvest tissues. The frozen tissues were sectioned and fixed with 10% formalin solution for H&E staining. For immunohistochemical study of the harvested tissues, the section was fixed with 4% paraformaldehyde (PFA), permeabilized by methanol treatment, and then incubated with primary antibody such as mouse anti-myosin heavy chain (MHC, MF20, hybridoma bank), rat anti-mouse CD31 (BD pharmingen), mouse anti-Pax7 (hybridoma bank) antibody, or anti-neurofilament (NF) antibody with α-bungarotoxin (BTX) staining, followed by secondary antibody such as Alexa 488 goat anti-mouse and FITC rabbit anti-rat antibody. For nuclei staining, the immunostained section was mounted with mounting medium containing propidium iodide (PI).

Histological and immunohistological studies clearly demonstrated that transplanted muscle fibers fragments re-assembled into fibers of the orientation of host muscle tissues and also showed that muscle stem cells (satellite cells) on the surface of transplanted fibers survived and proliferated, as evidenced by double staining of Vybrant staining and MHC or Pax7 immunostaining. Moreover, the integration of transplanted fibers with vascular network of host animals was confirmed by double staining of Vybrant staining and CD31 immunostaining. Innervation of implanted fibers with host animals was confirmed by triple staining of NF immunostaining and α-BTX staining including Vybrant staining.

Example 3

Comparison of Transplantation Efficiencies of Muscle Fiber Fragments, Long Fibers and Acellularized Tissue Components A study to compare the in vivo effect of decellularized fragments and fragments containing satellite cells was performed. Encouraged by the promising results from in vivo mouse study, an extended animal study using rats was performed in order to determine efficient engraftment of small fiber fragments when compared to that of long fibers using various injection volume and numbers of fiber fragments. Additionally, acellular fragments without cellular components were transplanted to examine possibility of their use as "off-the shelf" components for allogeneic transplantation. Muscle fiber fragments from rats (Lewis rats, 10-12 weeks) were isolated using the same protocols as described above for mice. Various volumes (100, 200, and 300 μL) of fiber fragments ($7 \times 10^4$ fibers/ml) were injected to gastrocnemius (GN) muscles without any muscle defects using a syringe with a 26 G needle. For a long fiber transplantation, 300 μL of fibers ($3 \times 10^3$ fibers/ml) (Hall J K et al, *Sci Transl Med* 2011) isolated without the process of filtration were injected. The injected numbers of long fibers were calculated based on the observation that one long fiber showed 1-3 mm in length. Acellular fragments were prepared by simple incubations in PBS without any chemical and enzymatic treatments. Briefly, isolated fiber fragments were incubated at 37° C. overnight and stored at 4° C. The elimination of cellular and DNA components were confirmed by Live/Dead (Invitrogen) cellular and nuclear staining on the fiber fragments. The transplantation of acellular fragments was done with 300 μL of fragment solution using same injection protocols above. At 1, 2, 3, and 4 weeks after transplantation, the GN muscle tissue was harvested, weighed, further processed for histological and immunohistological analysis. The area of engrafted fiber fragments was semi-quantified by measuring NIR positive areas in confocal images.

In comparison of muscle mass of GN tissue, injection of fiber fragments and acellular fragments induced an increase by a 5% in GN mass/body weight compared to that of sham, PBS, and long fibers, however there was no statistical differences. The localized fiber fragments were confirmed by NIR positive spots in the confocal images. In the groups of 300 μL injection of fiber fragments and acellular fragments, confocal images showed prominent engraftments of fiber fragments along the host muscle tissue, whereas long fibers did not, which strongly insist that fragmentation of muscle fibers promote efficient delivery of muscle fibers in vivo. Like the results of mouse study, the engrafted fiber fragments from rats were integrated with vascular and neural networks of the host animal. Interestingly, the injection of acellular fragments facilitated host cells recruitment to engrafted sites and also showed similar patterns with fiber fragments in efficient integration with the host animals, which is another a promising approach to allogeneic transplantation for functional muscle regeneration.

Example 4

Direct Injection of Muscle Fiber Fragments for Treatment of Muscle Atrophy

Figure 4A:
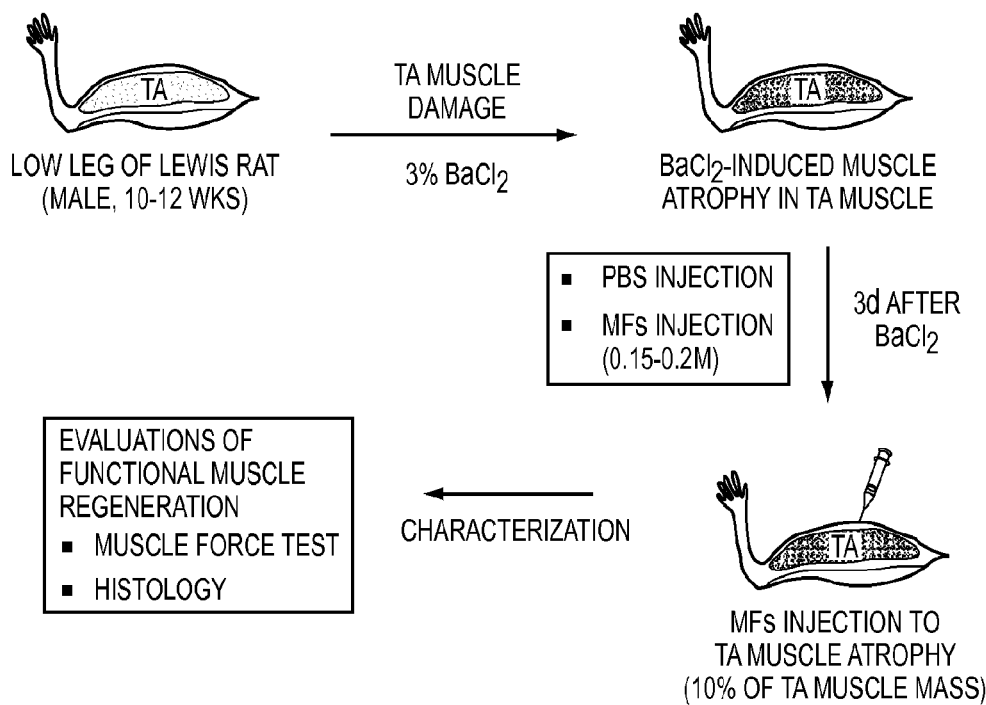
FIG. 4A is a schematic illustration of the application of muscle fiber fragment (MF) technology to a muscular atrophy model by injection of MF to chemically induced TA muscle injury in rats.

The objective of this study was to determine whether direct injection of muscle fiber fragments (MFs) could enhance muscle function restoration of muscular atrophy. It was hypothesized that the injected MFs would efficiently integrate with host muscle tissue as well as vascular and neural networks of the host and further improve functional muscle restoration of muscle injury. The overall study design is illustrated in FIG. 4A.

Figure 4B:
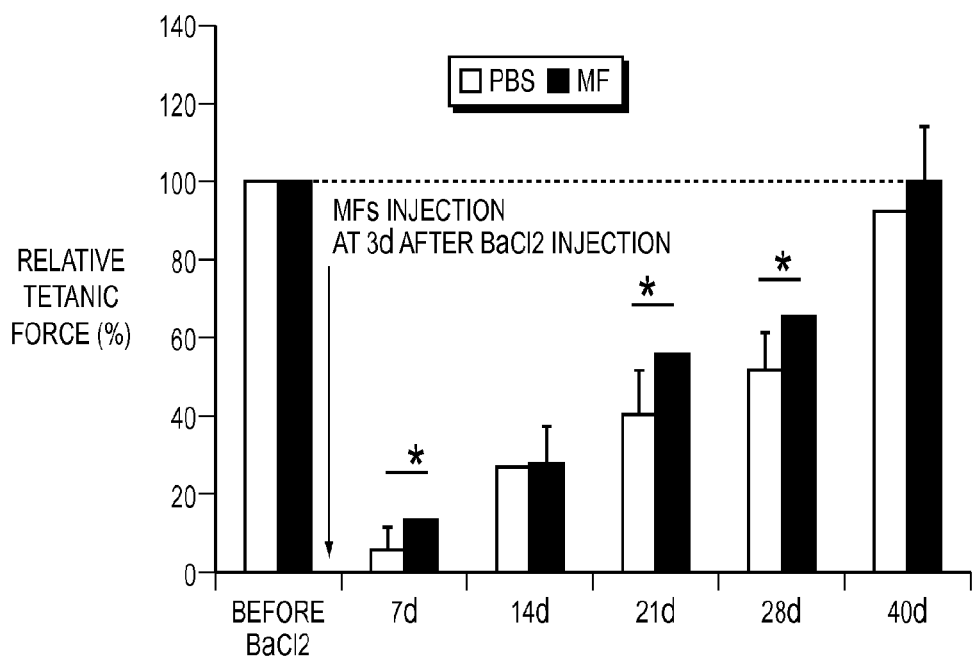
FIG. 4B is a graph showing that direct injection of MFs into TA muscle injury significantly enhanced muscle function at 7, 21, and 28 days (Student t-test, P<0.05, n=7, two independent experiments)

To create a muscle atrophy model in rats, 300 μl of 3% $BaCl_2$ was injected to one TA muscle. At 3 days after $BaCl_2$ injection, $0.15-0.2 \times 10^6$ MFs suspended in 300 μl of PBS solution were directly injected into the injured TA muscle using 26 G needle syringe. As controls, same volume of PBS solution was administrated. During animal study, functional muscle regeneration was evaluated by functional and morphological analysis. To determine functional muscle recovery, muscle force test was conducted at pre-determined time after MF injection. The isometric tetanic muscle force at 100 Hz of electrical stimulation was measured and the relative tetanic force (%) was calculated by normalizing a torque at each time point after the MF injection with that before injury. As shown in FIG. 4B, MF-injected TA muscle tissue showed higher relative tetanic force than control (PBS-injection) with statistically significant difference at 7, 21, and 28 days after MF injection.

Figure 5A:
FIGS. 5A-5D provide morphological analysis of the cells of the muscle atrophy study three weeks after injection, showing integration of injected MFs and MF-derived muscle progenitor cells (Pax7$^+$ cells) (FIG. 5B) with host muscle (FIG. 5A), vascular networks (FIG. 5C), and neural networks (FIG. 5D), Scale bar: 50 µm.
Figure 5B:
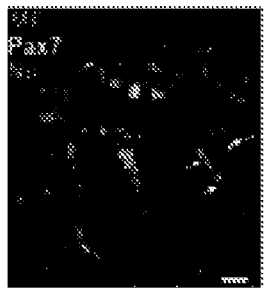
Figure 5C:
Figure 5D:
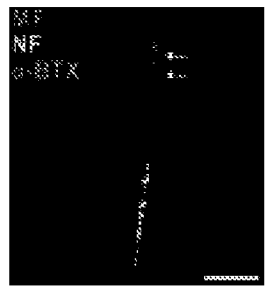

Morphological analysis using immunostaining of MF-injected TA muscle tissue [FIG. 5B] also supports improved muscle functions, demonstrating that the injected MFs efficiently integrated with host muscle tissues [FIG. 5A, myosin heavy chain (MHC)] as well as vascular [FIG. 5C, CD31] and neural networks [FIG. 5D, neurofilament (NF) & α-bungarotoxin (α-BTX)].

Example 5

Figure 6A:
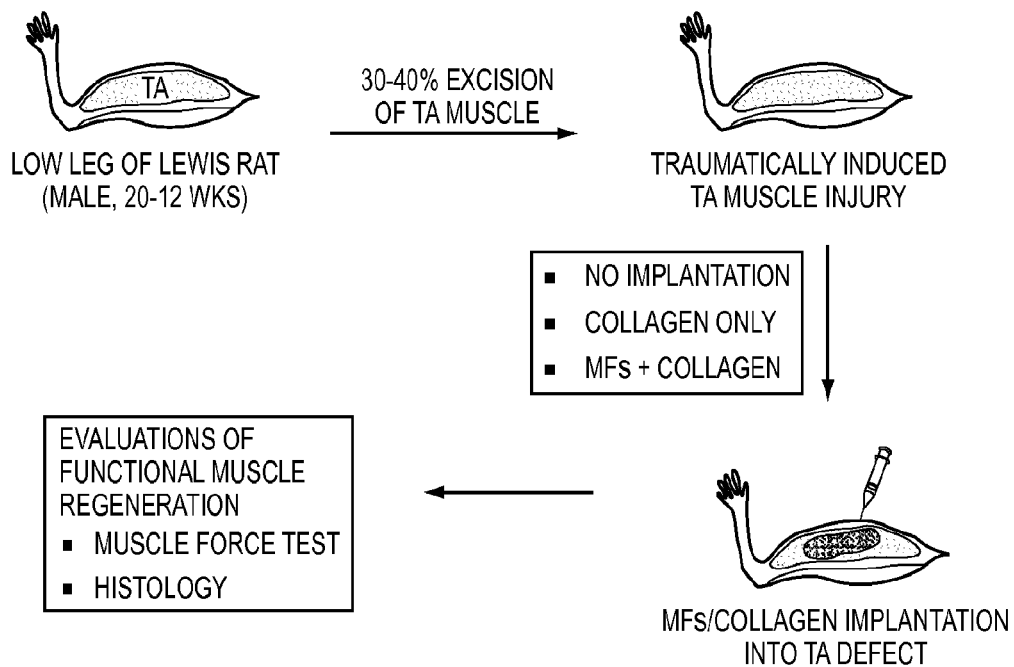
FIGS. 6A-6C illustrate the application of implantable MF-included construct to traumatic muscle defects model.

Implantation of Volumetric Construct Containing MFs for Treatment of Traumatic Muscle Defect The objective of this sub-study is to examine a feasibility of the implantation of 3-dimensional construct containing MFs for large muscle defect treatment. It was hypothesized that implantable construct containing MFs would maintain structural integrity and improve functional muscle restoration of surgically induced muscle defect. The overall study design is illustrated in FIG. 6A.

To create a traumatic muscle defect animal model, 30-40% of TA muscle tissue of rat was surgically excised. Total volume of MF/collagen construct (0.2 ml) [MFs (0.1 g≈0.1 ml) suspended in 0.1 ml of 0.8% collagen gel] was implanted to the muscle defect site and the implant was closed by suturing fascia and skin No implantation (defect only) and collagen only implantation were served as controls. At 7, 14, 21, and 28 days after implantation, tetanic force of TA was measured and the effect of MF/collagen construct implantation on the improved muscle function was determined by relative tetanic force (%).

Figure 6B:
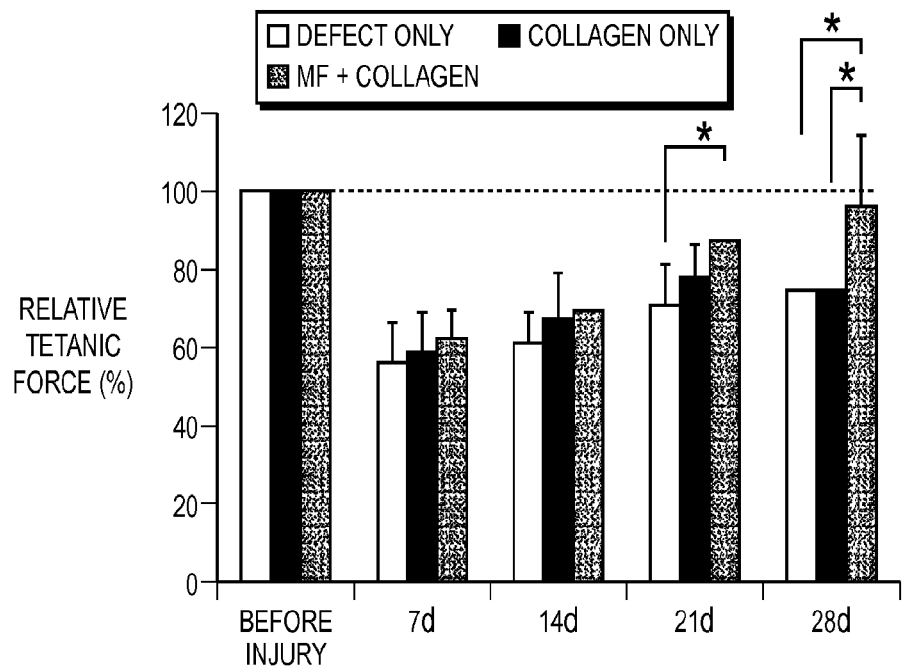
Figure 6C:
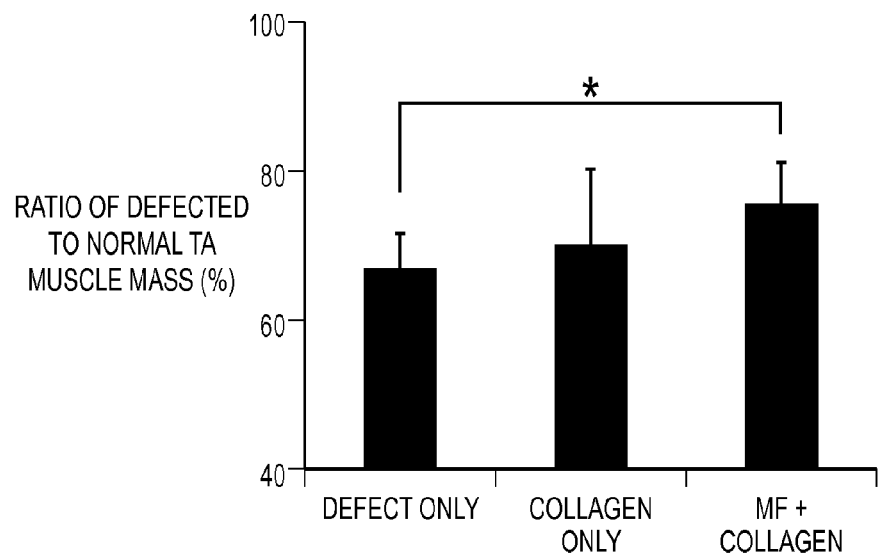

At each time point after implantation, MF/collagen implantation group showed higher relative tetanic force than that of defect only and collagen only. Particularly, the difference was statistically significant at 21 and 28 day (ANOVA and Tukey analysis, P<0.05) (FIG. 6B). Also, as shown in FIG. 6C, the implantation of the construct significantly improved muscle mass compared with defect only at 28 days after implantation. Our results show that the implantation of MF/collagen constructs into surgically induced muscle defect is feasible, successful, and induced enhanced muscle mass and function muscle restoration.

Example 6

Application of MF Technology to Urinary Sphincter Incontinence

Urinary incontinence (UI) is a major health issue that affects 1 in 3 individuals who have some loss of bladder control at some point in their lives. The market size of UI treatment is more than $20 billion and is expected to reach $30 billion by 2020. Current treatments includes biomaterial-derived mesh an sling implantation, however it often causes complications such as mesh erosions, obstructions of the urethra, injuries to adjacent organs, massive hemorrhage, damage to internal organs, scarring. Although cell therapy using muscle progenitor cells is a promising technique for UI treatment, it also has limitations in terms of requirement of cell manipulation and lengthy time before they can be used for therapy.

Figure 7A:
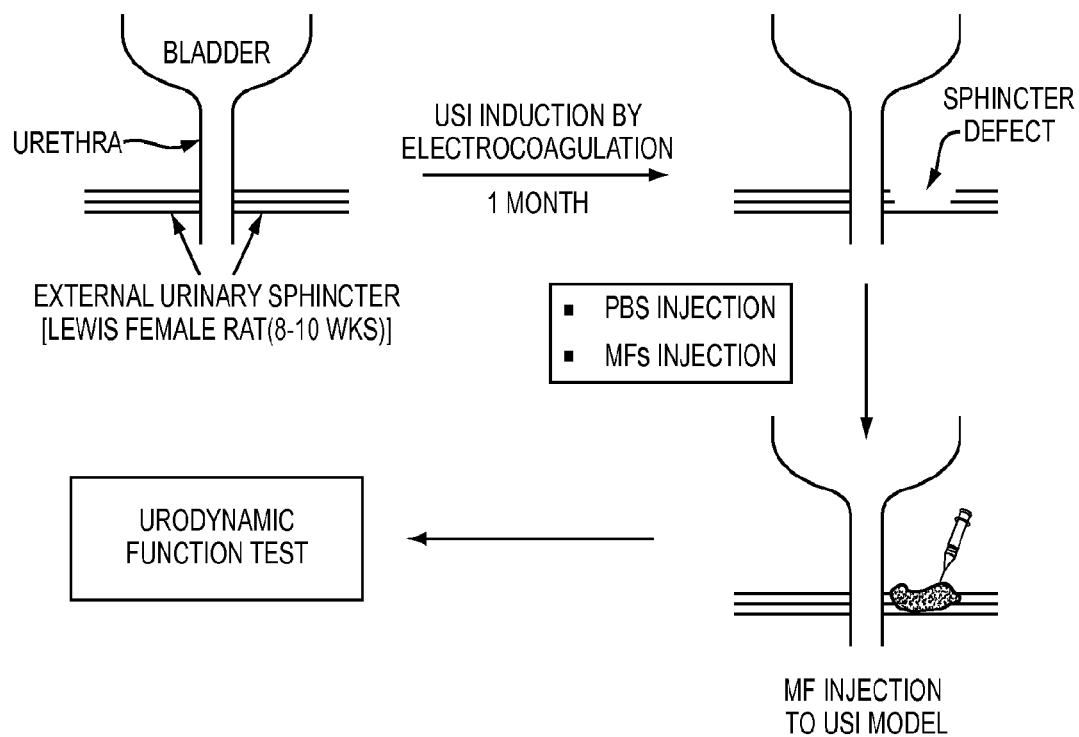
FIGS. 7A and 7B illustrate the application of MF technology to urinary sphincter incontinence (USI) model.
Figure 7B:
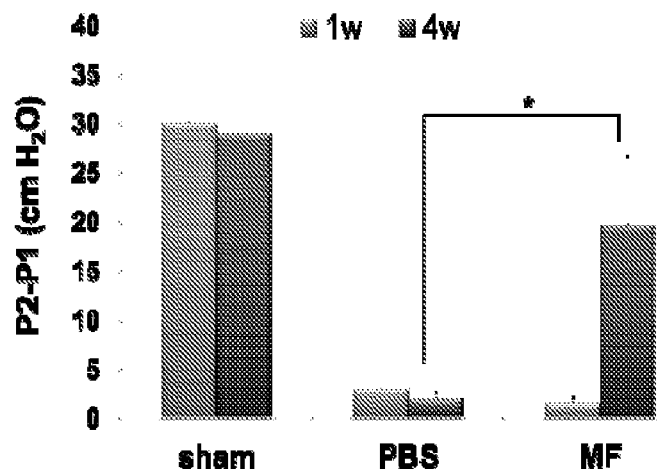

The objective of this study was to demonstrate the use of muscle fiber fragments for UI treatment. It was hypothesized that the injected MFs would integrate with the host muscle tissue in the damaged sphincter as well as vascular and neural networks of the host and further improve urodynamic function by enhancing sphincter skeletal muscle functions. The overall study design is described in FIG. 7A. To create urinary sphincter incontinence animal model, one side of the urethral sphincter of rats was injured by electro coagulation. At 1 month after sphincter injury, 0.05 g (≈0.05 ml) of MFs suspended in PBS solution was injected into the injured sphincter site. At 1 and 4 wks after MF injection, urethral sphincter contraction force was determined by measuring urine leak pressure without (P1) and with (P2) electrical stimulation. The results are tabulated in FIG. 7B. The difference between P2 and P1 is a maximal bladder pressure that external sphincter sustain. After sphincter injury, the electrical stimulation of the sphincters did not increase the leak point pressure of the bladder at any time points. However, in the MF injected group, the differential leak point pressure was 67% of normal value (sham group) at 1 month after MF injection with statistical difference (student t-test, P<0.01, n=3).

Example 7

Further Methods of Harvesting MFs

Figure 8A:
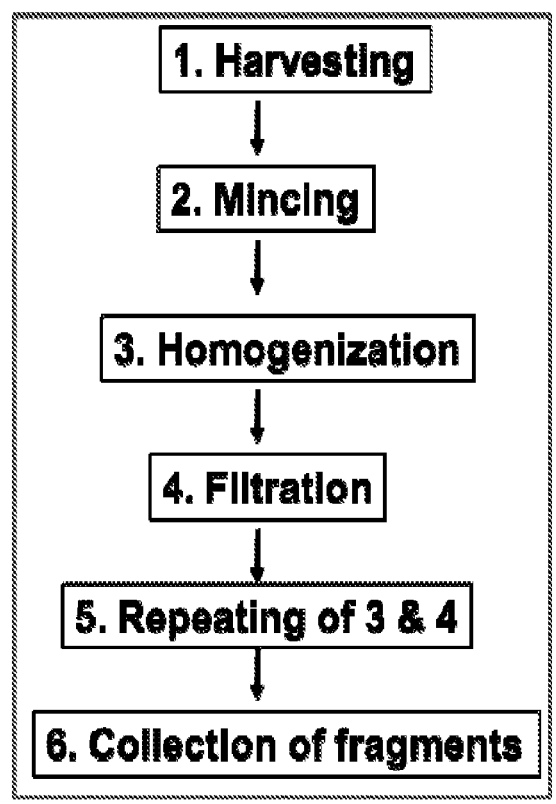
FIG. 8A illustrates an alternative technique for human muscle fiber fragments processing for clinical applications (≈30 min of processing time)
Figure 8B:
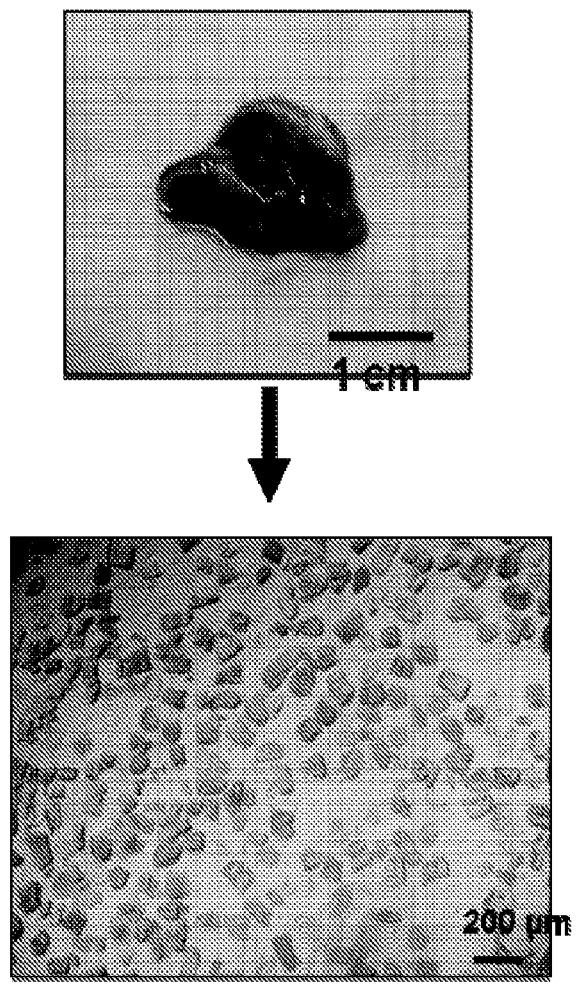
FIG. 8B is a micrograph showing the morphology of homogeneous and uniform sized human MFs and yield in weight (30-40%).

The goal of this study was to refine the human muscle fiber fragment process to improve yield, process time, and reagent utilization. FIG. 8A illustrated an alternative processing technique in which muscle tissue was harvested from the donor site, minced and then enzymatically homogenized with GMP grade collagenase solution (Liberase MNP-S, Roche). The product was then filtered and washed with Normosol (GMP grade saline solution). The steps of homogenization and filtration were repeated until homogeneous-sized MF fragments (e.g., 50-150 micrometers in diameter) were obtained. FIG. 8B is a microphotograph showing the resulting MFs, which were obtained with about 30 minutes of processing time and provided a 30-40% of yield in muscle weight.

All articles, papers, patents, patent applications and other publications cited herein are hereby incorporated by reference in their entirety.

What is claimed is:

1. A composition comprising:
   a population of muscle fiber fragments that are capable of reconstructing elongated muscle fibers from the fragments, and a scaffold,
   wherein the fragments exhibit cell wall rupture and have an average size of less than 100 µm, and further wherein the composition further includes viable satellite cells associated with at least some of the fragments,
   wherein the muscle fiber fragments are incorporated into the scaffold and
   wherein the scaffold is an injectable scaffold selected from the group of collagen gel, fibrin gel, alginate gel, or UV-induced crosslinkable gel system.

2. The composition of claim 1 wherein the composition is capable of orienting in alignment with native muscle fibers when implanted in a target muscle site.

3. The composition of claim 1, wherein the aspect ratio of the muscle fiber fragments is between 2:1 and 1:1.

4. The composition of claim 1, wherein at least 75% of the muscle fiber fragments exhibit cell wall rupture.

5. The composition of claim 1 wherein the composition further comprises a physiologically compatible fluid and the composition is formulated for injection.

6. The composition of claim 1 wherein the composition further comprises an adjuvant.

7. The composition of claim 6 wherein the adjuvant comprises at least one agent selected from the group of stem cells, muscle progenitor cells and growth factors.

8. The composition of claim 6 wherein the adjuvant comprises muscle progenitor cells.

9. The composition of claim 6 wherein the adjuvant comprises at least one growth factor selected from the group of: a bone morphogenic protein (BMP), a RUNX-2 protein, a LIM mineralization protein, a fibroblast growth factor, a platelet derived growth factor, an epidermal growth factor, an insulin-like growth factor, a transforming growth factor-a, a transforming growth factor-$\beta$, a nerve growth factor (NGF), a brain-derived neurotrophic factor (BDNF), a neuregulin (NRG), and agrin.

10. The composition of claim 1 wherein the injectable scaffold comprises a collagen gel.

11. The composition of claim 1 wherein the injectable scaffold comprises a fibrin gel.

12. The composition of claim 1 wherein the injectable scaffold comprises an alginate gel.

13. The composition of claim 1 wherein the injectable scaffold comprises a UV-induced crosslinkable gel system.

* * * * *